(12) United States Patent
Ghosh

(10) Patent No.: US 9,512,099 B2
(45) Date of Patent: Dec. 6, 2016

(54) COMPOUNDS FOR INHIBITION OF MEMAPSIN 1

(71) Applicant: Purdue Research Foundation, West Lafayette, IN (US)

(72) Inventor: Arun K. Ghosh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/485,389

(22) Filed: Sep. 12, 2014

(65) Prior Publication Data

US 2015/0080439 A1 Mar. 19, 2015

Related U.S. Application Data

(60) Provisional application No. 61/877,942, filed on Sep. 13, 2013.

(51) Int. Cl.
*C07D 277/30* (2006.01)
*C07D 317/60* (2006.01)
*C07C 311/08* (2006.01)
*C07C 233/78* (2006.01)

(52) U.S. Cl.
CPC ............ *C07D 317/60* (2013.01); *C07C 233/78* (2013.01); *C07C 311/08* (2013.01); *C07D 277/30* (2013.01)

(58) Field of Classification Search
CPC .................................................. C07D 277/30
See application file for complete search history.

(56) References Cited

FOREIGN PATENT DOCUMENTS

WO WO-2010/065861 A2 * 6/2010

OTHER PUBLICATIONS

Anderson, Robert N., "Deaths: Leading Causes for 1999", *National Vital Statistics Reports*, 49(11), (Oct. 12, 2001), 1-87.
De Strooper, Bart, et al., "Deficiencyof presenilin-1 inhibits the normal cleavage ofamyloid precursor protein", *Nature*, 391(6665), (1998), 387-390.
Lin, Xinli, et al., "Human aspartic protease memapsin 2 cleaves the β-secretase site of β-amyloid precursor protein", *Proc. Natl. Acad. Sci. USA*, 97(4), (2000), 1456-1460.
Selkoe, Dennis J., "Translating cell biology into therapeutic advances in Alzheimer's disease", *Nature*, 399(6738 Suppl.), (2000), 23-31.
Wild, Sarah, et al., "Global Prevalence of Diabetes—Estimates for the year 2000 and projections for 2030", *Diabetes Care*, 27, (2004), 1047-1053.

* cited by examiner

*Primary Examiner* — Laura L. Stockton
(74) *Attorney, Agent, or Firm* — Schwegman Lundberg & Woessner, P.A.

(57) ABSTRACT

Various embodiments of the present invention relate to, among other things, compounds that are inhibitors of Memapsin 1 and, as a result, are effective in the treatment of Alzheimer's disease or diabetes (e.g., Type 2 diabetes).

14 Claims, No Drawings

COMPOUNDS FOR INHIBITION OF MEMAPSIN 1

CROSS-REFERENCE TO RELATED APPLICATIONS

This application claims priority to U.S. Provisional Appl. Ser. No. 61/877,942, filed 13 Sep. 2013, the entire disclosure of which is incorporated by reference as if fully set forth herein.

STATEMENT OF GOVERNMENT SUPPORT

This invention was made with government support under grant AG018933 awarded by the National Institutes of Health. The government has certain rights in the invention.

BACKGROUND OF THE INVENTION

Memapsin 1 is a close homolog of memapsin 2, or beta-secretase (BACE), whose effect on beta-amyloid precursor protein (APP) leads to the production of beta-amyloid (A beta) peptide. BACE has been shown to play a role in the progression of Alzheimer's disease and type 2 diabetes, also known as diabetes melitus.

Briefly, 171 million individuals were estimated to have diabetes in the world, and this is expected to increase to 366 million by 2030. S. Wild et al., *Diabetes Care* 27: 1047-1053 (2004). It is no surprise, therefore, that diabetes represents a major illness and development of new effective treatments is of great importance.

Furthermore, Alzheimer's disease is a progressive, degenerative disorder that attacks the brain's nerve cells, or neurons, resulting in loss of memory, thinking and language skills, and behavioral changes. Alzheimer's disease accounts for the majority of senile dementias and is a leading cause of death in adults. Anderson, R. N., *Natl. Vital Stat. Rep.* 49:1-87 (2001). Histologically, the brain of persons afflicted with Alzheimer's disease is characterized by a distortion of the intracellular neurofibrils and the presence of senile plaques composed of granular or filamentous argentophilic masses with an amyloid protein core, largely due to the accumulation of β-amyloid peptide (Aβ) in the brain. Aβ accumulation plays a role in the pathogenesis and progression of the disease and is a proteolytic fragment of amyloid precursor protein (APP). Selkoe, D. J., *Nature* 399: 23-31 (1999). APP is cleaved initially by β-secretase followed by γ-secretase to generate Aβ. Lin, X., et al., *Proc. Natl. Acad. Sci. USA* 97:1456-1460 (2000); and De Stropper, B., et al., *Nature* 391:387-390 (1998).

Because of the large impact of diabetes and Alzheimer's on the world's population and the apparent paucity of therapeutic agents that treat both diseases by targeting (e.g., inhibiting) memapsin 1, there is a need for compounds designed for inhibiting memapsin 1.

DETAILED DESCRIPTION OF THE INVENTION

The various embodiments of the present invention provide, among other things therapeutic agents that are effective for the treatment of Alzheimer's disease and diabetes by targeting (e.g., inhibiting) mamapsin 1. These therapeutic agents include compounds of the general formula (Ia)-(Ic), collectively known as compounds of the general formula (I):

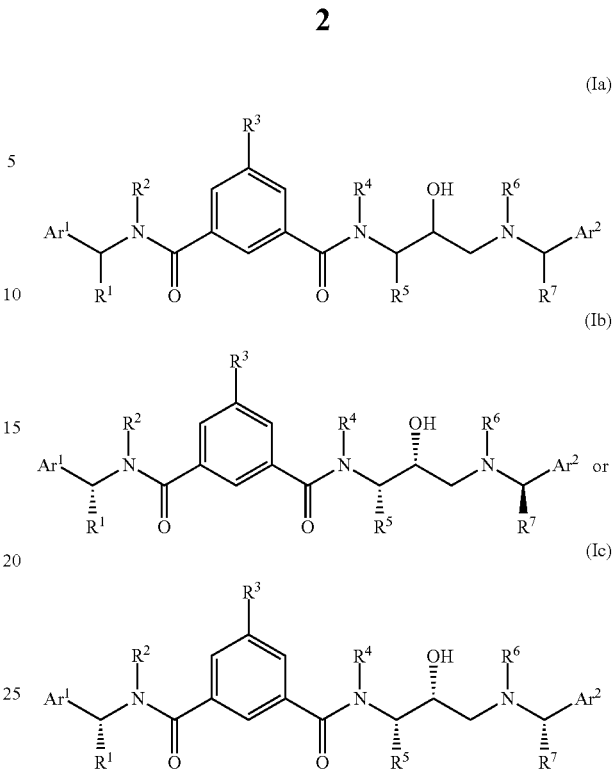

or a pharmaceutically acceptable salt, polymorph, prodrug, solvate or clathrate thereof,
wherein:
$Ar^1$ and $Ar^2$ are each independently substituted or unsubstituted aryl;
$R^1$ is hydrogen, alkyl or arylalkyl;
$R^2$, $R^4$, and $R^6$ are each, independently, hydrogen, substituted or unsubstituted alkyl, substituted or unsubstituted alkenyl or substituted or unsubstituted arylalkyl;
$R^3$ is hydrogen, substituted or unsubstituted alkyl or —$NR^8_2$ (wherein each $R^8$ is, independently, hydrogen, substituted or unsubstituted alkyl or substituted or unsubstituted arylalkyl or —$SO_2R^9$, wherein $R^9$ is hydrogen or substituted or unsubstituted alkyl); and
$R^5$ and $R^7$ are each independently hydrogen, substituted or unsubstituted alkyl or substituted or unsubstituted arylalkyl.

In some embodiments with regard to the compounds of the general formula (I), $Ar^1$ is substituted or unsubstituted phenyl. In other embodiments with regard to the compounds of the general formula (I), $Ar^2$ is substituted or unsubstituted phenyl. In still other embodiments, with regard to the compounds of the general formula (I), $Ar^1$ and $Ar^2$ are each substituted or unsubstituted phenyl. In yet other embodiments with regard to the compounds of the general formula (I), $Ar^1$ is unsubstituted phenyl and $Ar^2$ is substituted or unsubstituted phenyl, preferably substituted phenyl, such as phenyl substituted with one or more halogen (e.g., F), —$OCH_3$, ($C_1$-$C_4$) alkyl, or —$N((C_1$-$C_4)$ alkyl$)_2$ groups or two adjacent groups on the phenyl form a methylenedioxy (—O—$CH_2$—O—) or ethylenedioxy (—O—$CH_2$—$CH_2$—O—) group.

In some embodiments with regard to the compounds of the general formula (I), $R^1$ is substituted or unsubstituted alkyl. In other embodiments with regard to the compounds of the general formula (I), $R^1$ is unsubstituted alkyl. In still other embodiments with regard to the compounds of the general formula (I), $R^1$ is substituted or unsubstituted ($C_1$-$C_4$) alkyl, such as methyl, ethyl, n-propyl or isopropyl, preferably methyl.

In some embodiments with regard to the compounds of the general formula (I), $R^2$ is hydrogen, unsubstituted alkyl or unsubstituted alkenyl. In still other embodiments with regard to the compounds of the general formula (I), $R^2$ is hydrogen; unsubstituted ($C_1$-$C_4$) alkyl, such as methyl, ethyl, propyl or isopropyl, preferably methyl or n-propyl; or ($C_2$-$C_4$) alkenyl, such as propenyl.

In some embodiments with regard to the compounds of the general formula (I), $R^3$ is hydrogen, unsubstituted alkyl or —$NR^8_2$ (wherein each $R^8$ is, independently, hydrogen, substituted or unsubstituted alkyl or substituted or unsubstituted arylalkyl or —$SO_2R^9$, wherein $R^9$ is hydrogen or substituted or unsubstituted alkyl). In other embodiments with regard to the compounds of the general formula (I), $R^3$ is hydrogen; unsubstituted ($C_1$-$C_4$) alkyl, such as methyl, ethyl, propyl or isopropyl, preferably methyl; or —$NR^8_2$, wherein one $R^8$ group is unsubstituted ($C_1$-$C_4$) alkyl, such as methyl, ethyl, propyl or isopropyl, preferably methyl and the other $R^8$ group is —$SO_2R^9$, wherein $R^9$ is substituted or unsubstituted alkyl. In some embodiments, one $R^8$ group is unsubstituted ($C_1$-$C_4$) alkyl, such as methyl, ethyl, propyl or isopropyl, preferably methyl and the other $R^8$ group is —$SO_2R^9$, wherein $R^9$ is unsubstituted alkyl, such as unsubstituted ($C_1$-$C_4$) alkyl, such as methyl, ethyl, propyl or isopropyl, preferably methyl.

In some embodiments with regard to the compounds of the general formula (I), $R^4$ is hydrogen. In other embodiments with regard to the compounds of the general formula (I) $R^6$ is hydrogen. In still other embodiments with regard to the compounds of the general formula (I), at least one of $R^4$ and $R^6$ is hydrogen or $R^4$ and $R^6$ are both hydrogen.

In some embodiments with regard to the compounds of the general formula (I), $R^5$ is substituted or unsubstituted arylalkyl, such as substituted or unsubstituted aryl-($C_1$-$C_4$)-alkyl and ($C_6$-$C_{10}$)-aryl-($C_1$-$C_4$)-alkyl. In other embodiments with regard to the compounds of the general formula (I), $R^5$ is unsubstituted arylalkyl, such as unsubstituted aryl-($C_1$-$C_4$)-alkyl and ($C_6$-$C_{10}$)-aryl-($C_1$-$C_4$)-alkyl, wherein at least one of the aryl and the alkyl component is unsubstituted. In other embodiments with regard to the compounds of the general formula (I), $R^5$ is aryl-$CH_2$—, such as benzyl, wherein the aryl group is unsubstituted or substituted with halo (e.g., F). In other embodiments with regard to the compounds of the general formula (I), $R^5$ is phenyl-$CH_2$—, such as benzyl, wherein the phenyl group is unsubstituted or substituted with halo (e.g., F).

In some embodiments with regard to the compounds of the general formula (I), $R^7$ is hydrogen or substituted or unsubstituted alkyl, such as substituted or unsubstituted ($C_1$-$C_4$) alkyl. In some embodiments, $R^7$ is hydrogen or unsubstituted ($C_1$-$C_4$) alkyl, such as methyl, ethyl, propyl or isopropyl, preferably methyl.

In some embodiments, compounds of the general formula (I) include:

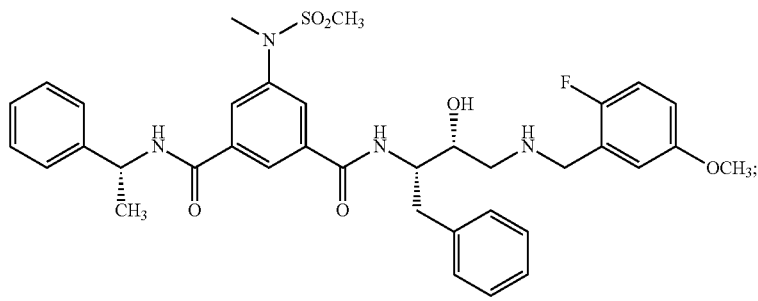

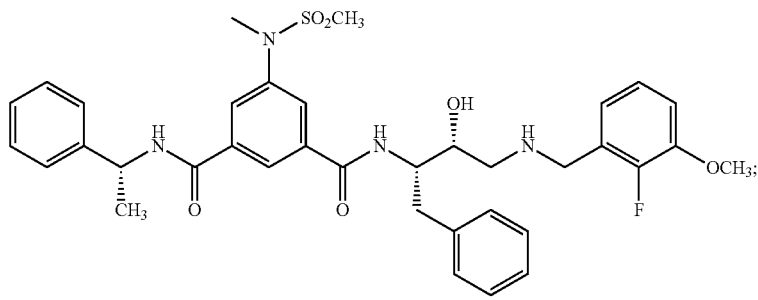

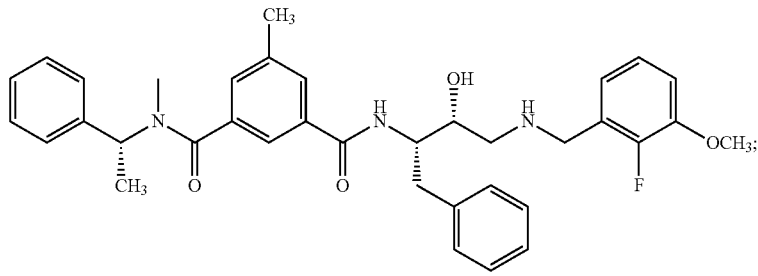

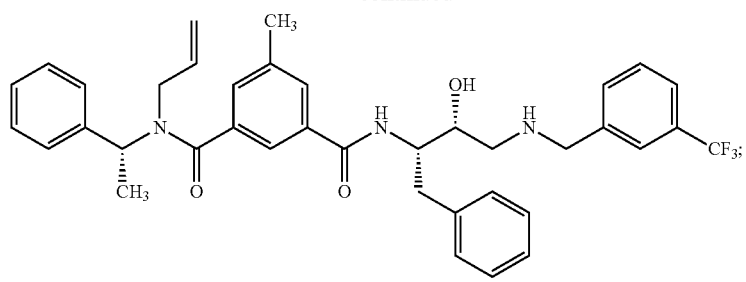
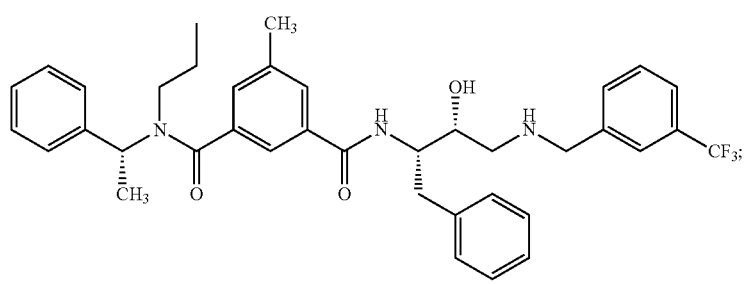
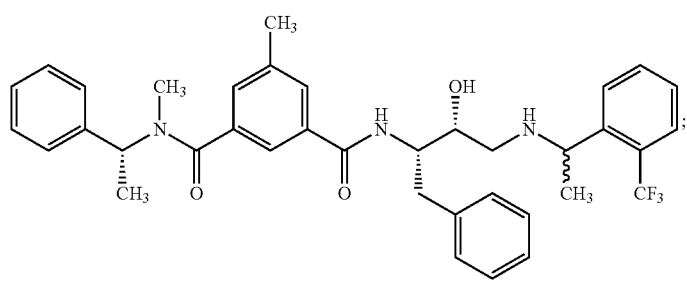
(e.g., dr = 1:1)
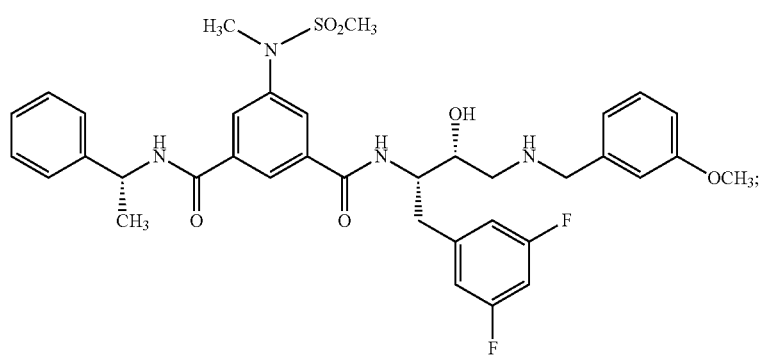
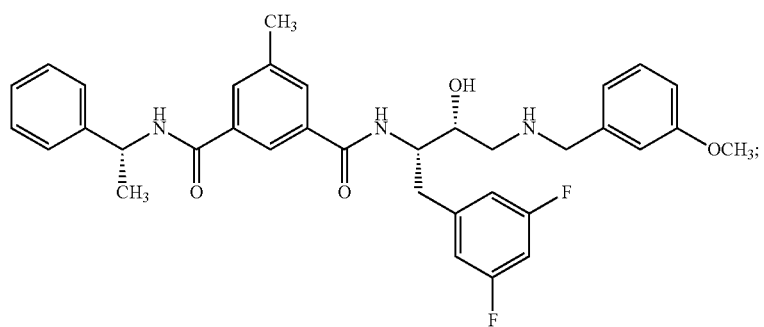

-continued
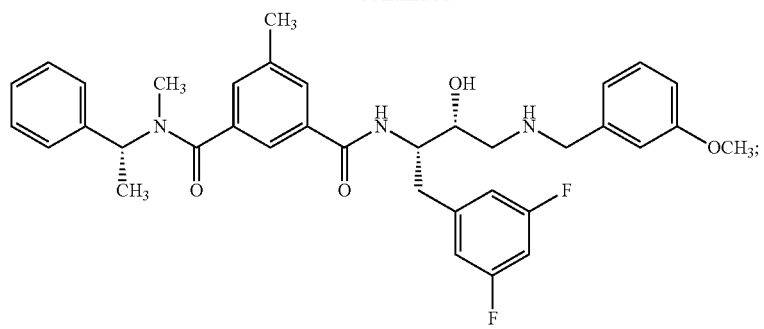
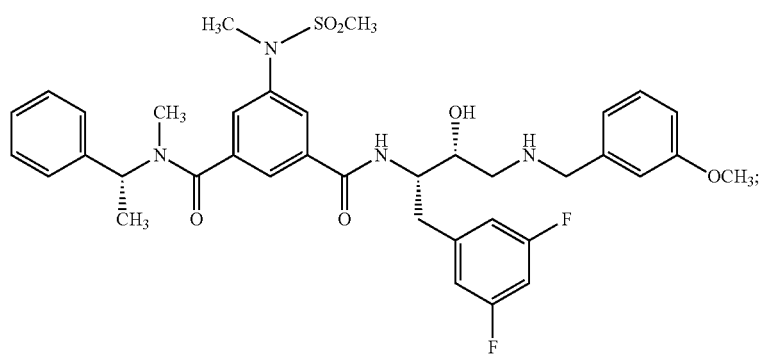
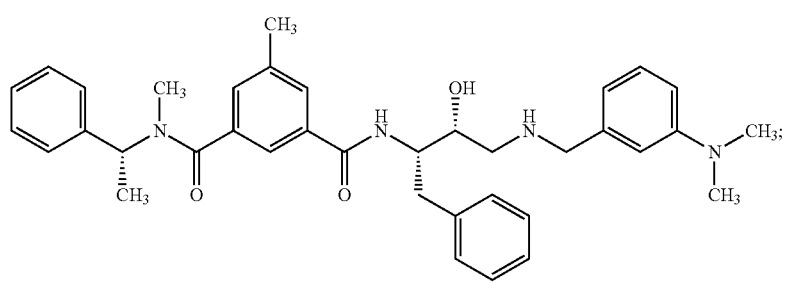
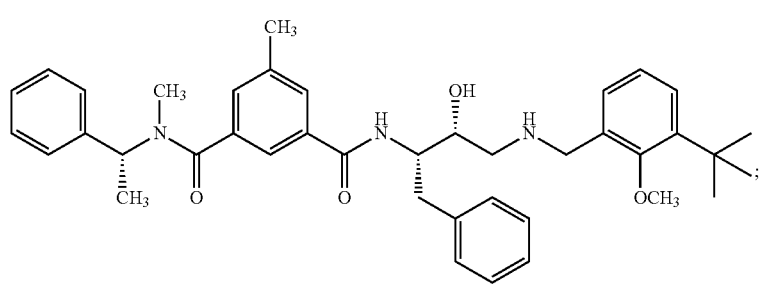
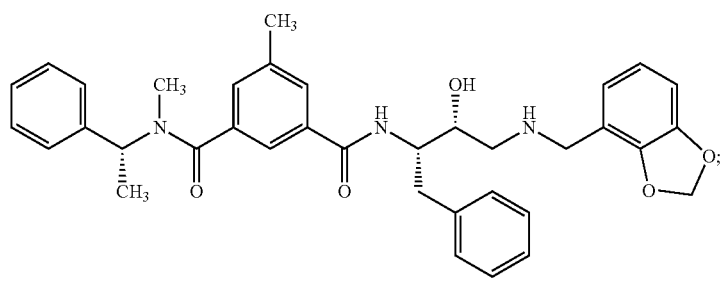

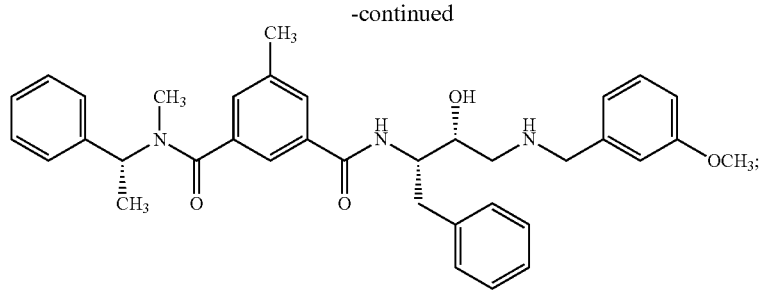

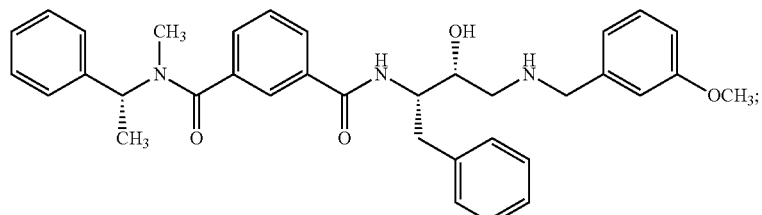

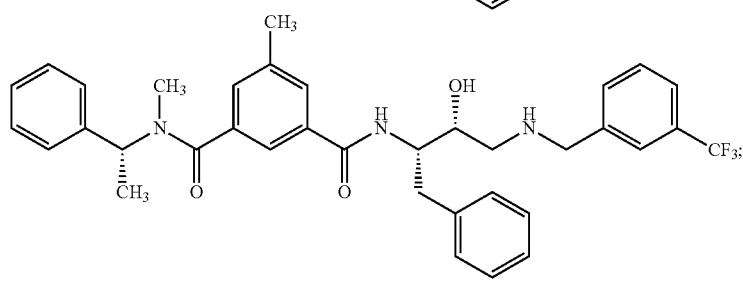

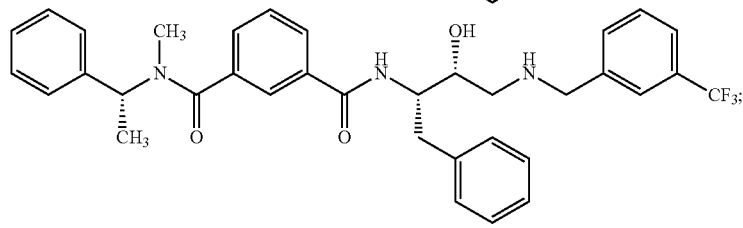

and pharmaceutically acceptable salts, polymorphs, prodrugs, solvates or clathrates thereof.

These therapeutic agents also include compounds of the general formula (IIa)-(IIc), collectively known as compounds of the general formula (II):

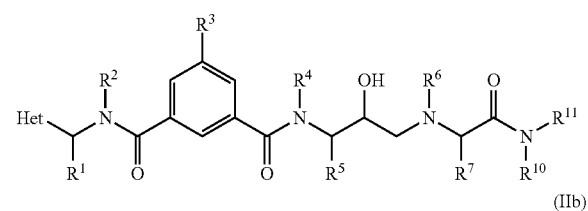
(IIa)

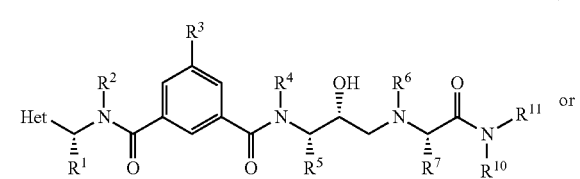
(IIb)

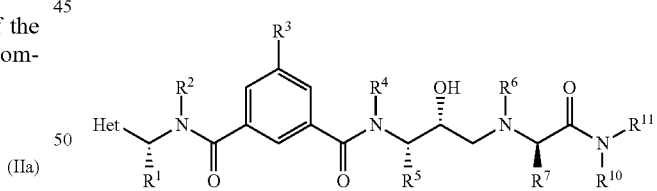
(IIc)

or a pharmaceutically acceptable salt, polymorph, prodrug, solvate or clathrate thereof,
wherein:
$R^1$-$R^7$ are defined herein;
Het represents a substituted or unsubstituted heterocycle; and
$R^{10}$ and $R^{11}$ are each independently hydrogen, substituted or unsubstituted alkyl, substituted or unsubstituted alkenyl or substituted or unsubstituted arylalkyl.

In some embodiments with regard to the compounds of the general formula (II), Het represents a substituted or unsubstituted 5-membered heterocycle, such as a substituted or unsubstituted thiazole. In some embodiments, when the 5-membered heterocycle is substituted, it is substituted with substituted or unsubstituted ($C_1$-$C_4$) alkyl, such as methyl, ethyl, n-propyl or isopropyl, preferably methyl.

In some embodiments with regard to the compounds of the general formula (II), $R^1$ is hydrogen.

In some embodiments with regard to the compounds of the general formula (II), $R^2$ is hydrogen or unsubstituted alkyl. In still other embodiments with regard to the compounds of the general formula (II), $R^2$ is hydrogen or unsubstituted ($C_1$-$C_4$) alkyl, such as methyl, ethyl, propyl or isopropyl, preferably methyl.

In some embodiments with regard to the compounds of the general formula (II), $R^3$ is hydrogen or unsubstituted alkyl. In other embodiments with regard to the compounds of the general formula (II), $R^3$ is hydrogen or unsubstituted ($C_1$-$C_4$) alkyl, such as methyl, ethyl, propyl or isopropyl, preferably methyl.

In some embodiments with regard to the compounds of the general formula (II), $R^4$ is hydrogen. In other embodiments with regard to the compounds of the general formula (II) $R^6$ is hydrogen. In still other embodiments with regard to the compounds of the general formula (II), $R^4$ and $R^6$ are both hydrogen.

In some embodiments with regard to the compounds of the general formula (II), $R^5$ is substituted or unsubstituted arylalkyl, such as substituted or unsubstituted aryl-($C_1$-$C_4$)-alkyl and ($C_6$-$C_{10}$)-aryl-($C_1$-$C_4$)-alkyl. In other embodiments with regard to the compounds of the general formula (II), $R^5$ is unsubstituted arylalkyl, such as unsubstituted aryl-($C_1$-$C_4$)-alkyl and ($C_6$-$C_{10}$)-aryl-($C_1$-$C_4$)-alkyl, wherein at least one of the aryl and the alkyl component is unsubstituted. In other embodiments with regard to the compounds of the general formula (II), $R^5$ is aryl-$CH_2$—, such as benzyl.

In some embodiments with regard to the compounds of the general formula (II), $R^7$ is substituted or unsubstituted alkyl, such as substituted or unsubstituted ($C_1$-$C_4$) alkyl. In some embodiments, $R^7$ is methyl, ethyl, propyl or butyl, preferably butyl. In some embodiments, $R^7$ is monohydroxy-substituted methyl, ethyl, propyl or butyl, preferably butyl.

In some embodiments with regard to the compounds of the general formula (II), $R^{10}$ and $R^{11}$ are each independently hydrogen or substituted or unsubstituted alkyl, such as substituted or unsubstituted ($C_1$-$C_4$) alkyl. In other embodiments, $R^{10}$ is hydrogen and $R^{11}$ is substituted or unsubstituted ($C_1$-$C_4$) alkyl, such as methyl, ethyl, propyl or isopropyl, preferably isopropyl.

In some embodiments, compounds of the general formula (II) include:

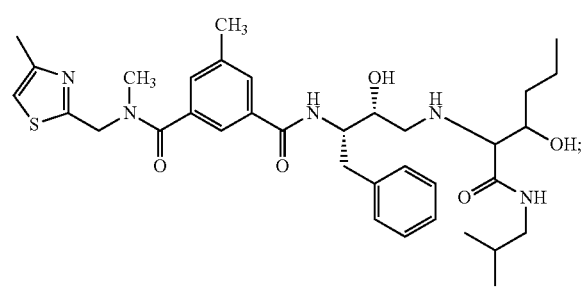

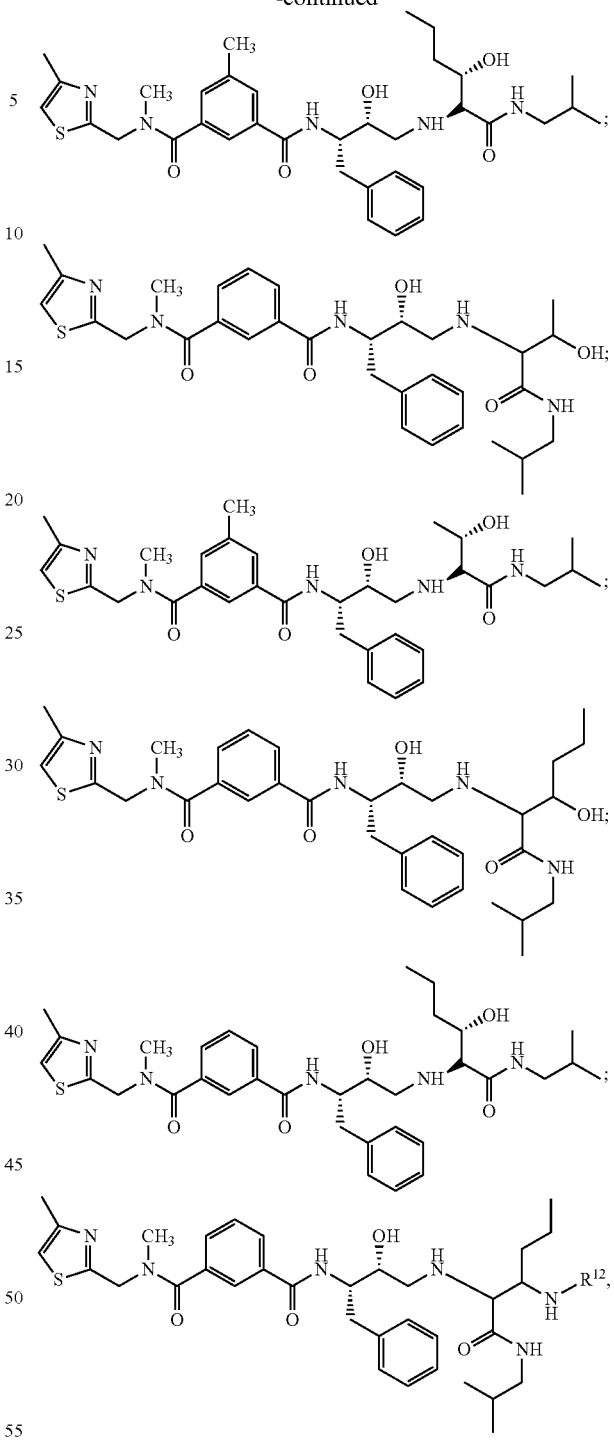

wherein $R^{12}$ is hydrogen, substituted or unsubstituted alkyl or substituted or unsubstituted arylalkyl;

and pharmaceutically acceptable salts, polymorphs, prodrugs, solvates or clathrates thereof.

Those of ordinary skill in the art will recognize that compounds described herein (e.g., the compounds of the general formula (I) and (II)) contain chiral centers. And even though, in some instances, specific diastereomers are given herein (e.g., the compounds of the formula (Ib), (Ic), (IIb), and (IIc)), all possible diastereomers of the compounds described herein are contemplated herein.

The term "alkyl" as used herein refers to substituted or unsubstituted straight chain and branched alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$) or from 1 to 4 carbon atoms ($C_1$-$C_4$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, and isopentyl groups. Representative substituted alkyl groups can be substituted one or more times with any of the groups listed herein, for example, amino, hydroxy, cyano, carboxy, nitro, thio, alkoxy, and halogen groups.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "alkenyl" as used herein refers to substituted or unsubstituted straight chain and branched alkenyl groups and cycloalkenyl groups having from 2 to 40 carbon atoms ($C_2$-$C_{40}$), 2 to about 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$). Examples of straight and branched chain alkenyl groups include, but are not limited to, those with from 2 to 8 carbon atoms such as vinyl (—CH=$CH_2$), —CH=CH($CH_3$), —CH=C($CH_3$)$_2$, —C($CH_3$)=$CH_2$, —C($CH_3$)=CH($CH_3$), —C($CH_2$$CH_3$)=$CH_2$, —$CH_2$CH=$CH_2$, —$CH_2$$CH_2$CH=$CH_2$, and the like. Examples of cycloalkenyl groups include, but are not limited to, cyclopentenyl, cyclohexenyl, and the like.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloarylalkyl)alkyl groups such as 4-ethyl-indanyl.

The term "heterocyclyl" or "heterocycle" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 5 to about 20 ring members, whereas other such groups have 5 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, thiazolyl, imidazolyl, triazyolyl, tetrazolyl, benzoxazolinyl, and benzimidazolinyl groups and the like.

The term "heteroarylalkyl" as used herein refers to alkyl groups as defined herein in which a hydrogen or carbon bond of an alkyl group is replaced with a bond to a heteroaryl group as defined herein.

The term "amine" as used herein refers to primary, secondary, and tertiary amines having, e.g., the formula N(group)$_3$ wherein each group can independently be H or non-H, such as alkyl, aryl, and the like. Amines include but are not limited to R—$NH_2$, for example, alkylamines, arylamines, arylalkylamines; $R_2$NH wherein each R is independently selected, such as dialkylamines, diarylamines, aralkylamines, heterocyclylamines and the like; and $R_3$N wherein each R is independently selected, such as trialkylamines, diarylalkylamines, alkyldiarylamines, triarylamines, and the like. The term "amine" also includes ammonium ions as used herein.

The terms "halo," "halogen," or "halide" group, as used herein, by themselves or as part of another substituent, mean, unless otherwise stated, a fluorine, chlorine, bromine, or iodine atom.

The term "substituted" as used herein refers to a group in which one or more hydrogen atoms contained therein are replaced by one or more non-hydrogen atoms. Examples of substituents include, but are not limited to, a halogen (e.g., F, Cl, Br, and I); an oxygen atom in groups such as hydroxyl groups, alkoxy groups, aryloxy groups, aralkyloxy groups; carboxyl groups (including carboxylic acids, carboxylates, and carboxylate esters); a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents, that can be bonded to a substituted carbon (or other) atom include F, Cl, Br, I, OR, $OC(O)N(R)_2$, CN, NO, $NO_2$, $ONO_2$, azido, $CF_3$, $OCF_3$, O (oxo), S (thiono), C(O), S(O), $N(R)_2$, SR, SOR, $SO_2R$, $SO_2N(R)_2$, $SO_3R$, C(O)R, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, $N(R)N(R)C(O)R$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, $C(=NH)N(R)_2$, C(O)N(OR)R, or C(=NOR)R wherein R can be hydrogen, alkyl, acyl, cycloalkyl, aryl, aralkyl, heterocyclyl, heteroaryl, or heteroarylalkyl; wherein two R groups bonded to a nitrogen atom or to adjacent nitrogen atoms can together with the nitrogen atom or atoms form a heterocyclyl, which can be mono- or independently multi-substituted; or wherein two R groups bonded to an oxygen atom or to adjacent oxygen atoms can together with the oxygen atom or atoms form a heterocyclyl, which can be mono- or independently multi-substituted, such as methylenedioxy (—O—$CH_2$—O—) or ethylenedioxy (—O—$CH_2$—$CH_2$—O—) group on, for example, an aryl group.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, heterocyclyl, heterocyclylalkyl, heteroaryl, heteroarylalkyl group or the like. In instances wherein the carbonyl carbon atom is bonded to a hydrogen, the group is a "formyl" group. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Various embodiments of the present invention also contemplate pharmaceutical compositions comprising one or more compounds of the various embodiments of the present invention (e.g. compounds of the general formula (I) and (II)) and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

In some embodiments, the various embodiments of the present invention contemplate compositions comprising a therapeutically effective amount of one or more compounds of the various embodiments of the present invention (e.g. compounds of the general formula (I) and (II)). In some embodiments, the compositions are useful in a method for treating Alzheimer's diseases or type 2 diabetes comprising administering a therapeutically effective amount of one or more compounds of the various embodiments of the present invention. In some aspects, the various embodiments of the present invention contemplate compounds of the general formula (I) and (II) for use as a medicament for treating a patient in need of relief from Alzheimer's disease or type 2 diabetes or conditions directly or peripherally associated with Alzheimer's disease and conditions associated with type 2 diabetes (e.g., hyperglycemia and resulting from the combination of resistance to insulin action, inadequate insulin secretion, and excessive or inappropriate glucagon secretion).

The term "therapeutically effective amount" as used herein, refers to that amount of one or more compounds of the various embodiments of the present invention (e.g. compounds of the general formula (I) and (II)) that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

The following embodiments are provided, the number of which is not to be construed as designating levels of importance:

Embodiment 1 relates to a compound of the formula (Ia)-(Ic):

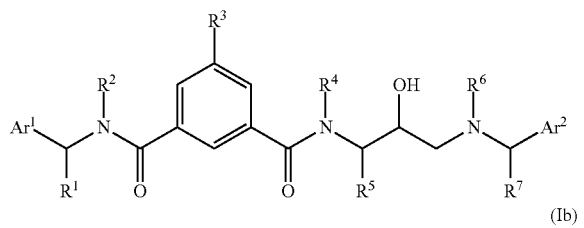
(Ia)

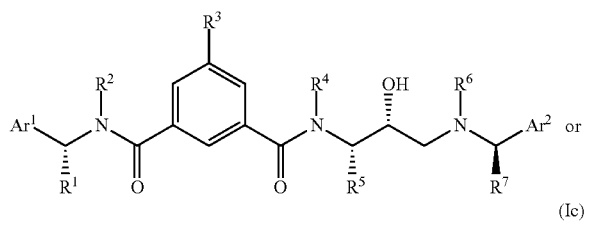
(Ib)

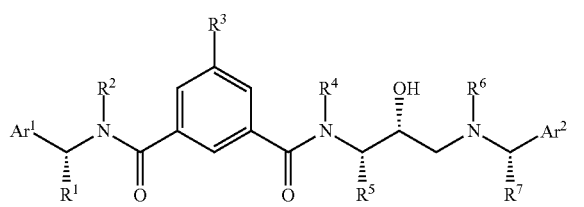
(Ic)

or a pharmaceutically acceptable salt, polymorph, prodrug, solvate or clathrate thereof, wherein:

$Ar^1$ and $Ar^2$ are each independently substituted or unsubstituted aryl;

$R^1$ is hydrogen, alkyl or arylalkyl;

$R^2$, $R^4$, and $R^6$ are each, independently, hydrogen, substituted or unsubstituted alkyl, substituted or unsubstituted alkenyl or substituted or unsubstituted arylalkyl;

$R^3$ is hydrogen, substituted or unsubstituted alkyl or —$NR^8_2$ (wherein each $R^8$ is, independently, hydrogen, substituted or unsubstituted alkyl or substituted or unsubstituted arylalkyl or —$SO_2R^9$, wherein $R^9$ is hydrogen or substituted or unsubstituted alkyl); and $R^5$ and $R^7$ are each independently hydrogen, substituted or unsubstituted alkyl or substituted or unsubstituted arylalkyl.

Embodiment 2 relates to the compound of Embodiment 1, wherein $Ar^1$ is substituted or unsubstituted phenyl and $Ar^2$ is substituted or unsubstituted phenyl.

Embodiment 3 relates to the compound of Embodiment 1, wherein $Ar^1$ is unsubstituted phenyl and $Ar^2$ is substituted or unsubstituted phenyl.

Embodiment 4 relates to the compound of Embodiments 1-3, wherein $Ar^2$ is substituted phenyl.

Embodiment 5 relates to the compound of Embodiments 1-4, wherein $R^1$ is substituted or unsubstituted ($C_1$-$C_4$) alkyl.

Embodiment 6 relates to the compound of Embodiments 1-5, wherein $R^1$ is methyl.

Embodiment 7 relates to the compound of Embodiments 1-6, wherein $R^2$ is hydrogen; unsubstituted ($C_1$-$C_4$) alkyl; or ($C_2$-$C_4$) alkenyl.

Embodiment 8 relates to the compound of Embodiments 1-7, wherein $R^3$ is hydrogen, unsubstituted alkyl or —$NR^8_2$ (wherein each $R^8$ is, independently, hydrogen, substituted or unsubstituted alkyl or substituted or unsubstituted arylalkyl or —$SO_2R^9$, wherein $R^9$ is hydrogen or substituted or unsubstituted alkyl).

Embodiment 9 relates to the compound of Embodiments 1-8, wherein one $R^8$ group is unsubstituted ($C_1$-$C_4$) and the other $R^8$ group is —$SO_2R^9$, wherein $R^9$ is unsubstituted alkyl.

Embodiment 10 relates to the compound of Embodiments 1-9, wherein at least one of $R^4$ and $R^6$ is hydrogen.

Embodiment 11 relates to the compound of Embodiments 1-10, wherein $R^5$ is substituted or unsubstituted ($C_6$-$C_{10}$)-aryl-($C_1$-$C_4$)-alkyl.

Embodiment 12 relates to the compound of Embodiments 1-11, wherein $R^7$ is hydrogen or substituted or unsubstituted ($C_1$-$C_4$) alkyl.

Embodiment 13 relates to the compound of Embodiments 1-12, selected from the group consisting of:

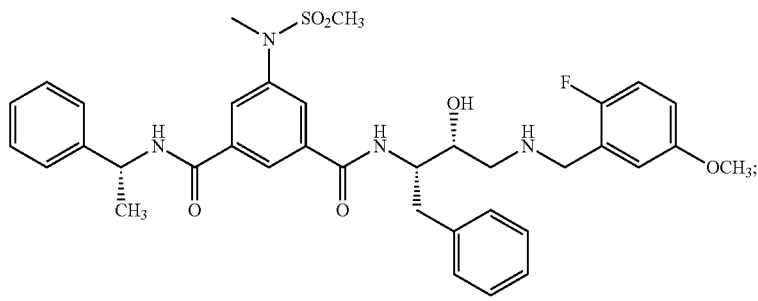

-continued
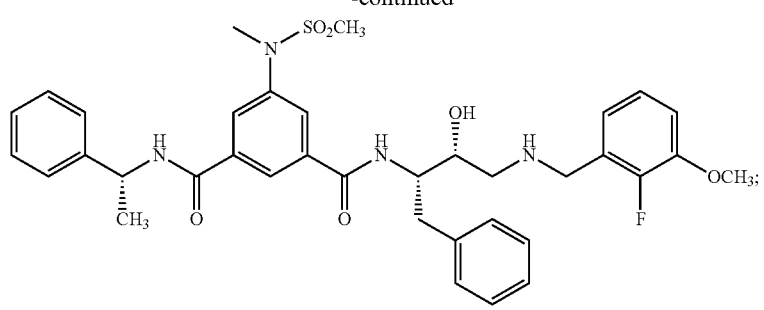
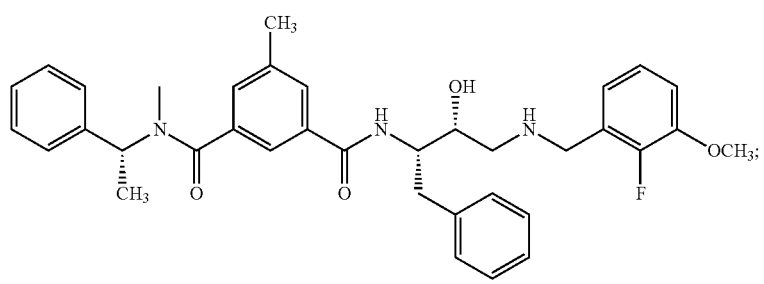
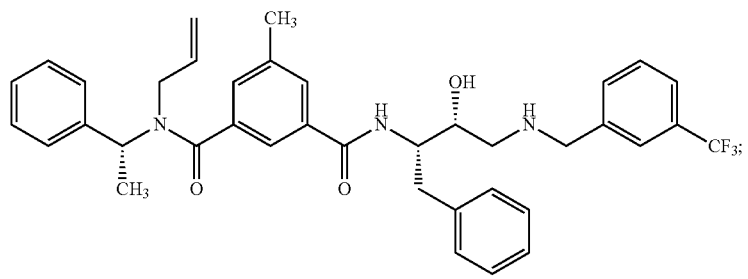
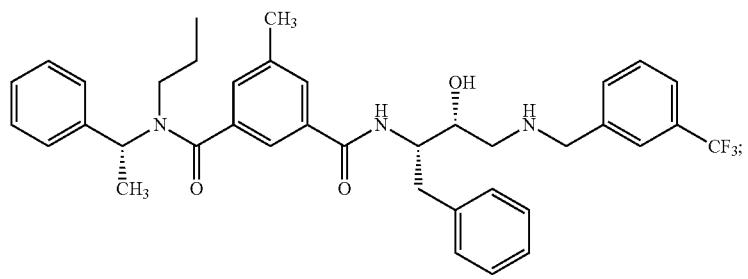
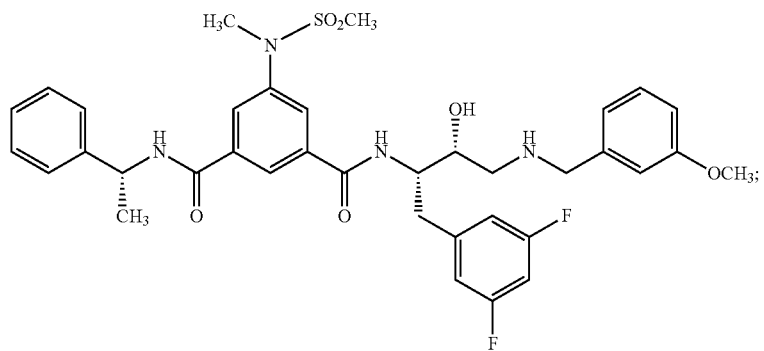

-continued
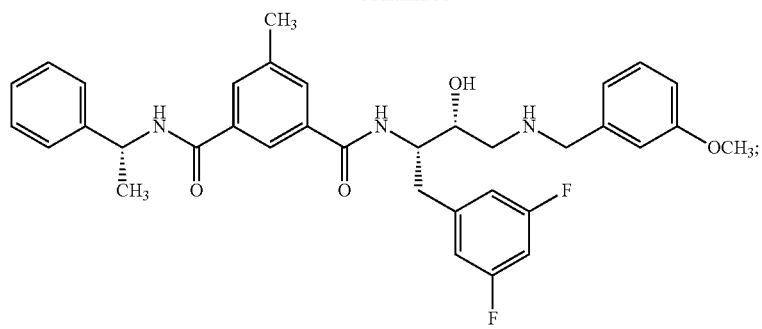
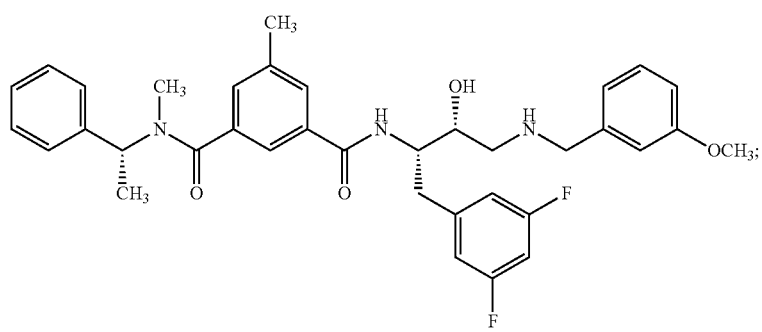
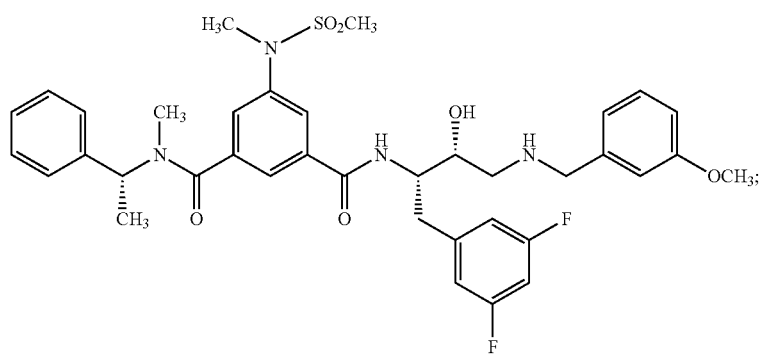
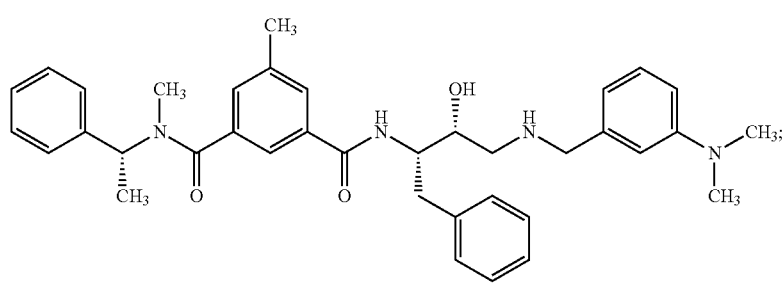
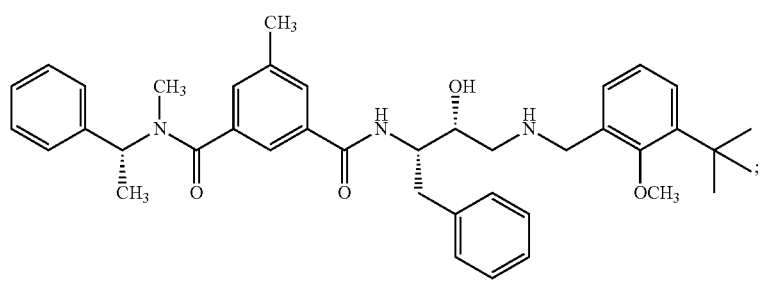

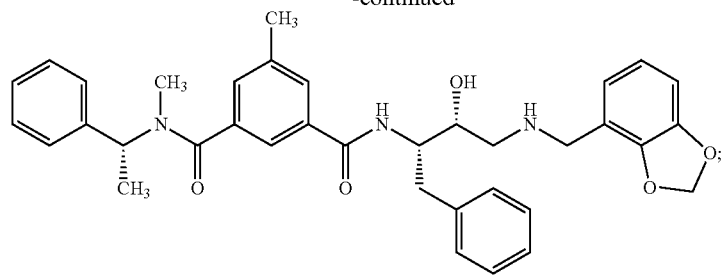
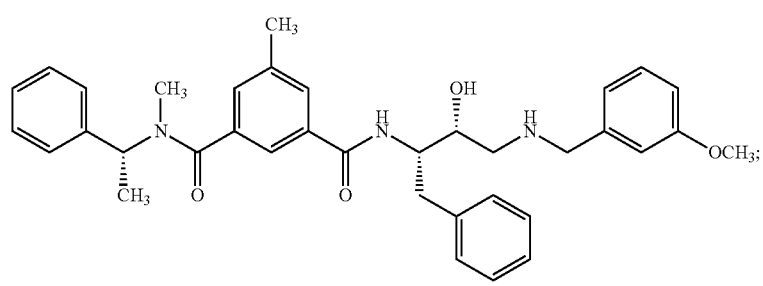
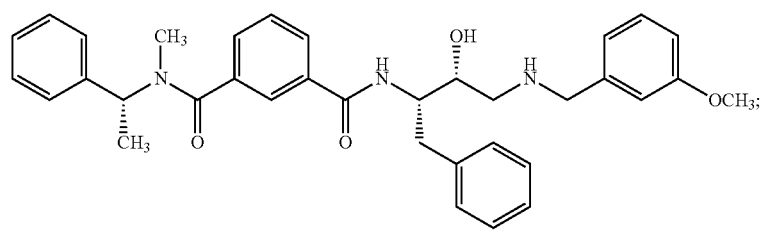
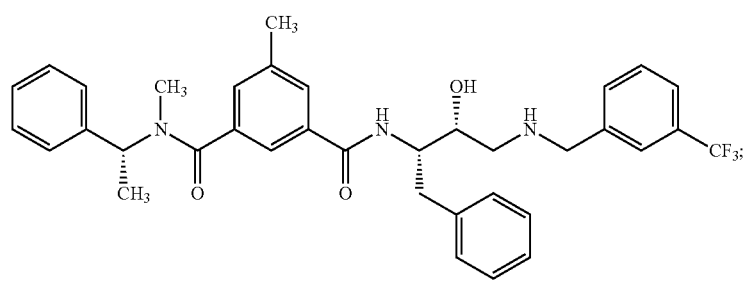
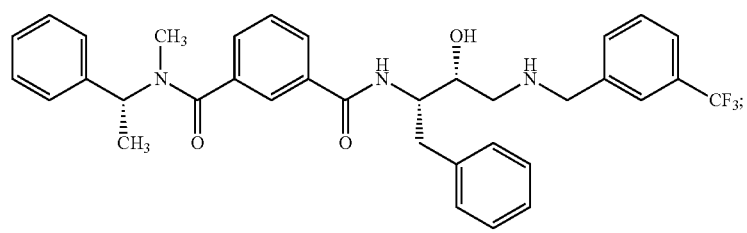

and pharmaceutically acceptable salts, polymorphs, prodrugs, solvates or clathrates thereof.

Embodiment 14 relates to a compound of the formula (IIa)-(IIc):

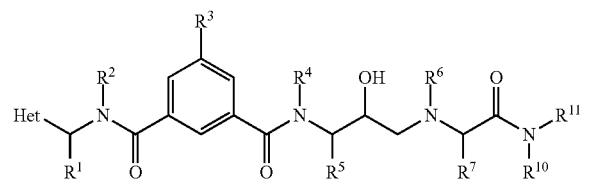

(IIa)

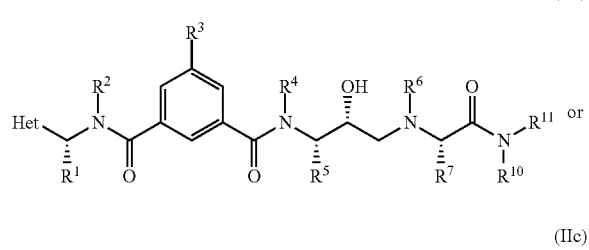

(IIb)

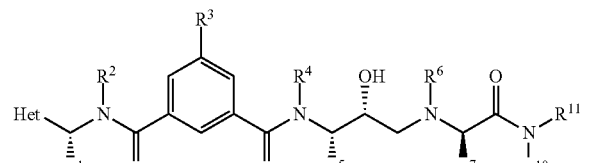

(IIc)

or a pharmaceutically acceptable salt, polymorph, prodrug, solvate or clathrate thereof,
wherein:
$R^1$ is hydrogen, alkyl or arylalkyl;
$R^2$, $R^4$, and $R^6$ are each, independently, hydrogen, substituted or unsubstituted alkyl, substituted or unsubstituted alkenyl or substituted or unsubstituted arylalkyl;
$R^3$ is hydrogen, substituted or unsubstituted alkyl or —$NR^8{}_2$ (wherein each $R^8$ is, independently, hydrogen, substituted or unsubstituted alkyl or substituted or unsubstituted arylalkyl or —$SO_2R^9$, wherein $R^9$ is hydrogen or substituted or unsubstituted alkyl);
$R^5$ and $R^7$ are each independently hydrogen, substituted or unsubstituted alkyl or substituted or unsubstituted arylalkyl; Het represents a substituted or unsubstituted heterocycle; and
$R^{10}$ and $R^{11}$ are each independently hydrogen, substituted or unsubstituted alkyl, substituted or unsubstituted alkenyl or substituted or unsubstituted arylalkyl.

Embodiment 15 relates to the compound of Embodiment 14, wherein Het represents a substituted or unsubstituted 5-membered heterocycle.

Embodiment 16 relates to the compound of Embodiments 14-15, wherein Het represents a substituted or unsubstituted thiazole.

Embodiment 17 relates to the compound of Embodiments 14-16, wherein $R^1$ is hydrogen.

Embodiment 18 relates to the compound of Embodiments 14-17, wherein $R^2$ is hydrogen or unsubstituted ($C_1$-$C_4$) alkyl.

Embodiment 19 relates to the compound of Embodiments 14-18, wherein $R^3$ is hydrogen or unsubstituted alkyl.

Embodiment 20 relates to the compound of Embodiments 14-19, wherein at least one of $R^4$ and $R^6$ is hydrogen.

Embodiment 21 relates to the compound of Embodiments 14-20, wherein $R^5$ is substituted or unsubstituted ($C_6$-$C_{10}$)-aryl-($C_1$-$C_4$)-alkyl.

Embodiment 22 relates to the compound of Embodiments 14-21, wherein $R^7$ is hydrogen or substituted or unsubstituted ($C_1$-$C_4$) alkyl.

Embodiment 23 relates to the compound of Embodiments 14-22, wherein $R^7$ is OH-substituted ($C_1$-$C_4$) alkyl.

Embodiment 24 relates to the compound of Embodiments 14-23, wherein $R^7$ is $NHR^{12}$-substituted ($C_1$-$C_4$) alkyl, wherein $R^{12}$ is hydrogen, substituted or unsubstituted alkyl or substituted or unsubstituted arylalkyl.

Embodiment 25 relates to the compound of Embodiment 14-24, wherein $R^{10}$ is hydrogen and $R^{11}$ is substituted or unsubstituted ($C_1$-$C_4$) alkyl.

Embodiment 26 relates to the compound of Embodiments 14-25 selected from the group consisting of:

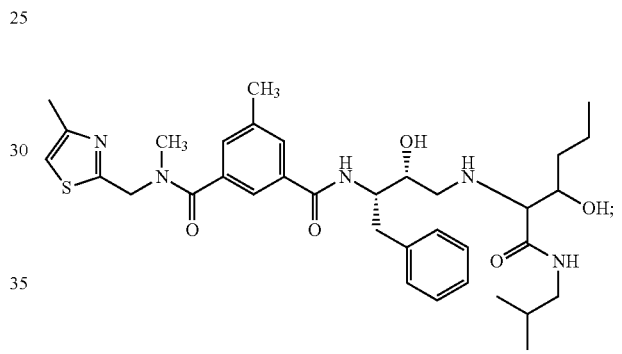

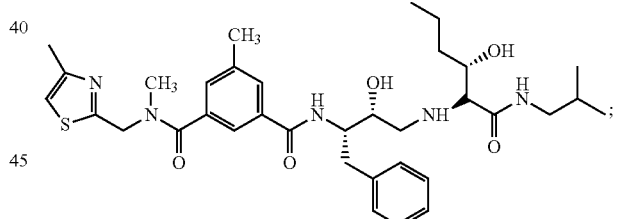

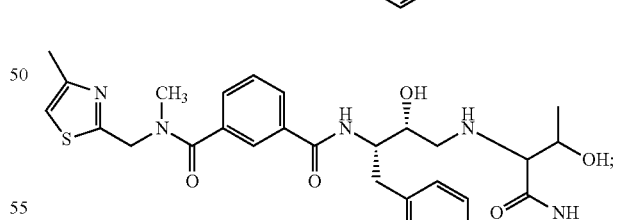

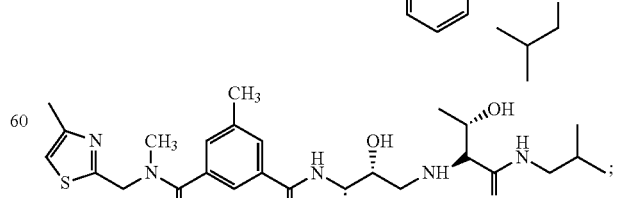

-continued

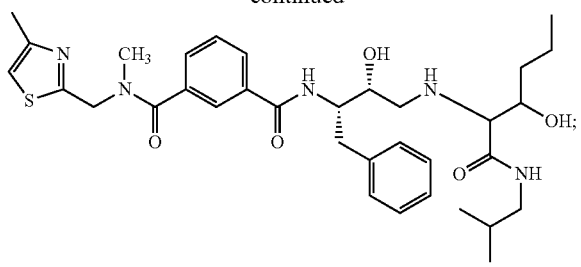

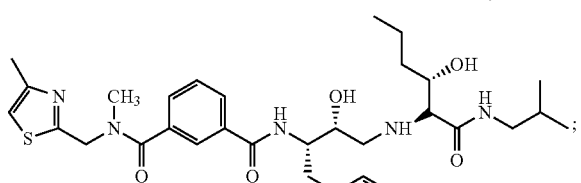

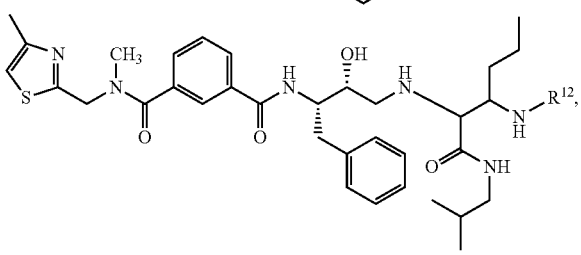

wherein R¹² is hydrogen, substituted or unsubstituted alkyl or substituted or unsubstituted arylalkyl; and pharmaceutically acceptable salts, polymorphs, prodrugs, solvates or clathrates thereof.

Embodiment 27 relates to a pharmaceutical composition comprising one or more compounds of Embodiments 1-13 and one or more pharmaceutically acceptable carriers, diluents, excipients or combinations thereof.

Embodiment 28 relates to a pharmaceutical composition comprising one or more compounds of Embodiments 14-28 and one or more pharmaceutically acceptable carriers, diluents, excipients or combinations thereof.

What is claimed is:

1. A compound of the formula (IIa)-(IIc):

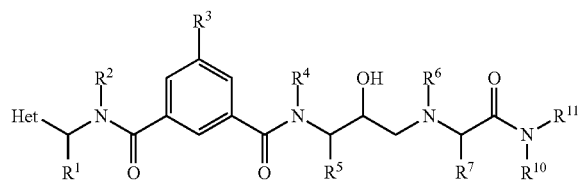
(IIa)

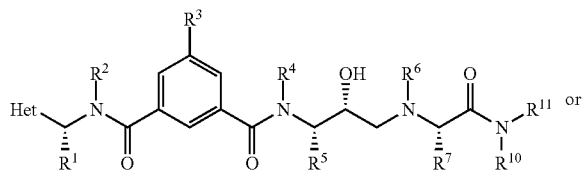
(IIb)

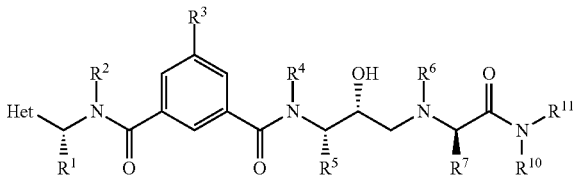
(IIc)

or a pharmaceutically acceptable salt, polymorph, prodrug, solvate or clathrate thereof,
wherein:
$R^1$ is hydrogen, alkyl or arylalkyl;
$R^2$, $R^4$, and $R^6$ are each, independently, hydrogen, substituted or unsubstituted alkyl, substituted or unsubstituted alkenyl or substituted or unsubstituted arylalkyl;
$R^3$ is hydrogen, substituted or unsubstituted alkyl or —$NR^8_2$ (wherein each $R^8$ is, independently, hydrogen, substituted or unsubstituted alkyl or substituted or unsubstituted arylalkyl or —$SO_2R^9$, wherein $R^9$ is hydrogen or substituted or unsubstituted alkyl);
$R^5$ and $R^7$ are each independently hydrogen, substituted or unsubstituted alkyl or substituted or unsubstituted arylalkyl;
Het represents a substituted or unsubstituted heterocycle; and
$R^{10}$ and $R^{11}$ are each independently hydrogen, substituted or unsubstituted alkyl, substituted or unsubstituted alkenyl or substituted or unsubstituted arylalkyl.

2. The compound of claim 1, wherein Het represents a substituted or unsubstituted 5-membered heterocycle.

3. The compound of claim 1, wherein Het represents a substituted or unsubstituted thiazole.

4. The compound of claim 1, wherein $R^1$ is hydrogen.

5. The compound of claim 1, wherein $R^2$ is hydrogen or unsubstituted ($C_1$-$C_4$) alkyl.

6. The compound of claim 1, wherein $R^3$ is hydrogen or unsubstituted alkyl.

7. The compound of claim 1, wherein at least one of $R^4$ and $R^6$ is hydrogen.

8. The compound of claim 1, wherein $R^5$ is substituted or unsubstituted ($C_6$-$C_{10}$)-aryl-($C_1$-$C_4$)-alkyl.

9. The compound of claim 1, wherein $R^7$ is hydrogen or substituted or unsubstituted ($C_1$-$C_4$) alkyl.

10. The compound of claim 9, wherein $R^7$ is OH-substituted ($C_1$-$C_4$) alkyl.

11. The compound of claim 9, wherein $R^7$ is $NHR^{12}$-substituted ($C_1$-$C_4$) alkyl, wherein $R^{12}$ is hydrogen, substituted or unsubstituted alkyl or substituted or unsubstituted arylalkyl.

12. The compound of claim 1, wherein $R^{10}$ is hydrogen and $R^{11}$ is substituted or unsubstituted ($C_1$-$C_4$) alkyl.

13. The compound of claim 1 selected from the group consisting of:

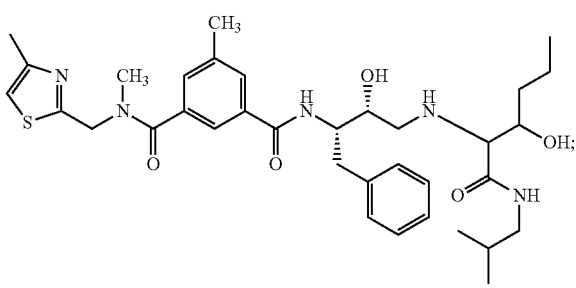

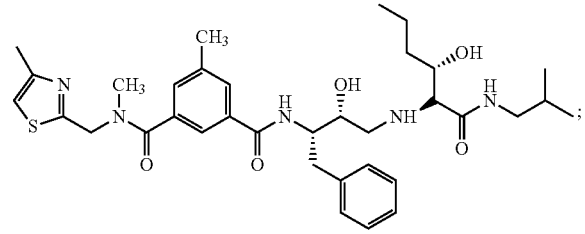

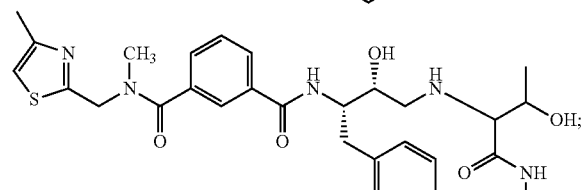

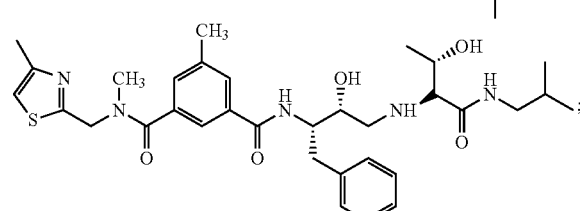

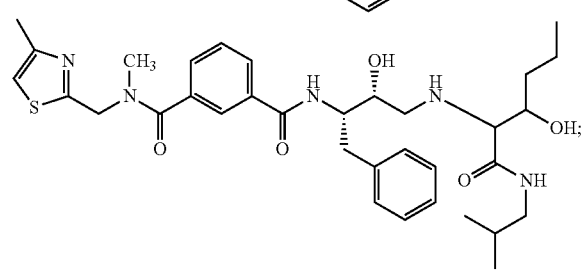

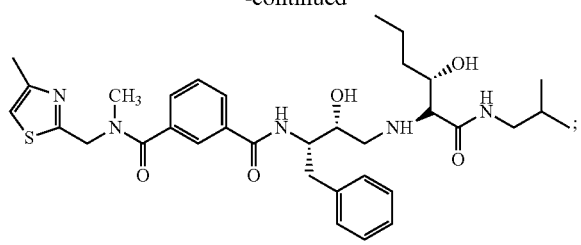

and

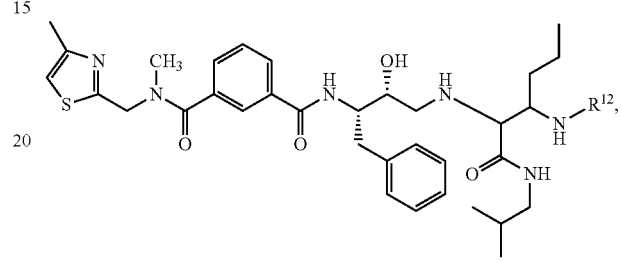

wherein $R^{12}$ is hydrogen, substituted or unsubstituted alkyl or substituted or unsubstituted arylalkyl; and pharmaceutically acceptable salts, polymorphs, prodrugs, solvates or clathrates thereof.

14. A pharmaceutical composition comprising one or more compounds of claim 1 and one or more pharmaceutically acceptable carriers, diluents, excipients or combinations thereof.

* * * * *